(12) United States Patent
Mehlem et al.

(10) Patent No.: US 6,767,992 B1
(45) Date of Patent: Jul. 27, 2004

(54) METHOD FOR PRODUCING L-PROLYL-L-M-SARCOLYSYL-L-P-FLUOROPHENYLALANINE AND DERIVATIVES THEREOF

(75) Inventors: Francesco Mehlem, Worblaufen (CH); Pietro Di Vittorio, Milan (IT)

(73) Assignee: PTC Pharma AG, Bern (CH)

( * ) Notice: Subject to any disclaimer, the term of this patent is extended or adjusted under 35 U.S.C. 154(b) by 0 days.

(21) Appl. No.: 09/831,816

(22) PCT Filed: Nov. 19, 1998

(86) PCT No.: PCT/CH98/00498

§ 371 (c)(1),
(2), (4) Date: Jul. 30, 2001

(87) PCT Pub. No.: WO00/31119

PCT Pub. Date: Jun. 2, 2000

(51) Int. Cl.$^7$ ................................................ C07K 5/08
(52) U.S. Cl. ........................ 530/331; 514/152; 552/164; 424/573
(58) Field of Search ........................... 514/152; 552/64; 424/573; 260/112.5

(56) References Cited

U.S. PATENT DOCUMENTS 3,814,746 A * 6/1974 De Barbieri ............. 260/112.5

FOREIGN PATENT DOCUMENTS

| BE | 775775 | 3/1992 | |
|---|---|---|---|
| FR | 2094175 | 2/1972 | |
| FR | 2101226 | 3/1972 | |
| WO | 9420136 | 9/1994 | |
| WO | WO 99/02177 | * 1/1999 | .......... A61K/38/06 |

OTHER PUBLICATIONS

Rajewski et al, "Pharmaceutical Applications of Cyclodextrins. 2. In Vivo Drug Delivery", Journal of Pharmaceutical Sciences, vol. 85, No. 11, pp. 1142–1169, Nov. 1996.

Astaldi, "Peptichemio: A Multifaceted Antiblastic Drug", Wadley Medical Bulletin, vol. 5, No. 3, pp. 303–326 (1975).

Hansson et al, "Cytotoxicity and DNA Cross–Linking Induced By Peptide Conjugated m–L–Sarcolysin In Human Melanoma Cells", Anticancer Research, vol. 11, pp. 1725–1730 (1991).

Hug et al, "A Phase II Study of Peptichemio In Advanced Breast Cancer", Cancer, vol. 45, pp. 2524–2528 (1980).

Medina et al, "Chlorpheniramine Inhibits The Synthesis of Ornithine Decarboxylase and the Proliferation of Human Breast Cancer Cell Lines", Breast Cancer Research and Treatment, vol. 35, pp. 187–194 (1995).

US Patent Application Publication 2003/0162721 to Mehlem et al, published Aug. 28, 2003 (Ser. No. 09/462,155; International Filing Date Jul. 7, 1998; 102(e) date Jan. 5, 2000).

* cited by examiner

*Primary Examiner*—Christopher Tate
*Assistant Examiner*—Roy Teller
(74) *Attorney, Agent, or Firm*—Stevens, Davis, Miller & Mosher, LLP

(57) ABSTRACT

L-prolyl-L-m-sarcolysyl-L-p-fluorophenylalanine, lower alkyl esters and/or acid addition salts thereof are produced. For this purpose, L-p-fluorophenylalanine with a protected carboxyl group is caused to react with L-m-sarcolysine with a protected amino group preferably with cooling in an anhydrous medium in the presence of dicyclohexylcarbodiimid, L-m-sarcolysyl-L-p-fluorophenylalanine with a protected amino group and a protected carboxyl group being obtained. Then the amino protection group is removed, with formation of L-m-sarcolysyl-L-p-fluorophenylalanine with a protected carboxyl group. The obtained product is caused to react with proline with a protected amino group in the presence of dicyclohexylcarbodiimid. L-prolyl-L-m-sarcolysyl-L-p-fluorophenylalanine with a protected amino group is obtained. Finally, the amino protection group is removed, and optionally the lower alkyl ester group is removed and/or the obtained compound is converted into an acid addition salt.

14 Claims, No Drawings

METHOD FOR PRODUCING L-PROLYL-L-M-SARCOLYSYL-L-P-FLUOROPHENYLALANINE AND DERIVATIVES THEREOF

The present invention relates to a method for producing a pharmaceutically active peptide compound, which contains L-m-sarcolysine as the amino acid component. The active substance serves particularly for chemotherapy against cancers and is used especially for melanomas. In using a carrier substance on a cyclodextrin basis, the active substance is released delayed, which makes possible a sufficient bioavailability during a sufficiently long period of time.

A complex of six peptides containing m-L-sarcolysine has become known under the trade name "Peptichemio" (Insituto Sieroterapico Milanese S. Belfanti, Milan, Italy) for chemotherapy against cancer. It has been found that the activity of the individual peptides is different and that particularly one representative exhibits very high toxicity to melanoma cells. The peptides are a development which began with the product "Melphalan," i.e., 4-[bis(2-chloroethyl)]-amino-L-phenylalanine. It has been found that this product has a cytostatic effect and can be utilized both for myeloma and for melanoma therapy. For the further development of the active substance, derivatives of the product were prepared. This also resulted in the L-m-sarcolysine [=m-{di-2-chlorethyl}amino}-L-phenylalanine], which was further derived in that peptides were prepared which contained the modified amino acid as a component. A combination of the six oligopeptides L-seryl-L-p-fluorophenylalanyl-L-m-sarcolysyl ethyl ester; L-prolyl-L-m-sarcolysyl-L-p-fluorophenylalanine ethyl ester; L-m-sarcolysyl-N-nitro-L-arginyl-L-norvaline ethyl ester; L-p-fluorophenylalanyl-L-m-sarcolysyl-L-asparagine ethyl ester; <sic. L-p->fluorophenylalanyl-glycyl-L-m-sarcolysyl-norvaline ethyl ester and L-m-sarcolysyl-L-arginyl-L-lysyl-L-m-sarcolysyl-L-histidine methyl ester formed the active principle of the antitumor agent "Peptichemio." Of the six peptides, the L-prolyl-L-m-sarcolysyl-L-p-fluorophenylalanine (PSF) and its lower alkyl esters have proven particularly suitable.

It has been found that PSF showed considerably higher cytotoxicity compared with peptichemio itself (R. Levenson, et al., Radiumhemmet, Karolinska Hospital, Stockholm, Sweden, Eur. J. Cancer Clin. Oncol.; 23: 6, 783–788, 1987). According to these studies, it has been found that the peptide L-propyl-m-sarcolysyl-L-p-fluorophenylalanine (PSF) was 35 times and 28 times, respectively, more toxic to RPMI 8322 melanoma cells than melphalan and m-sarcolysine, respectively. Similar differences between the active substances have also been found for other melanoma cell lines.

It is the object of the present invention to make available a method of producing PSF that makes possible an economical and safe production of the active substance.

Production of such a compound is described in the printed publications BE-A-775775 and U.S. Pat. No. 3,814,746. The described production takes place according to the following schema 1:

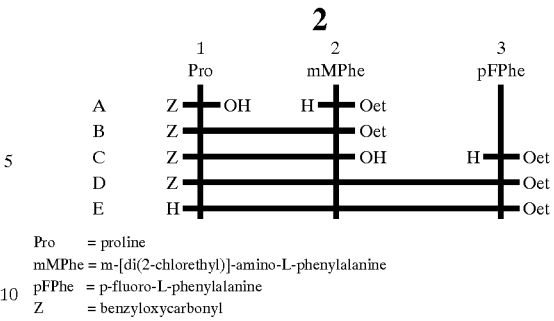

Pro = proline
mMPhe = m-[di(2-chlorethyl)]-amino-L-phenylalanine
pFPhe = p-fluoro-L-phenylalanine
Z = benzyloxycarbonyl The above schema shows, in step A, the condensation of the N-carbobenzoxy-L-proline with the ethyl ester of m-[di-(2-chlorethyl)-amino]-L-phenylalanine, the corresponding protected peptide resulting, as is shown in step B in schema 1.

In step C, the N-carbobenzoxy-L-prolyl-m-[di-(2-chlorethyl)-amino]-L-phenylalanine is obtained from the N-carbobenzoxy-L-prolyl-m-[di-(2-chlorethyl)-amino]-L-phenylalanine ethyl ester, and subsequently the condensation of this compound is carried out with p-fluoro-L-phenylalanine ethyl ester, while in step D of the schema 1 the carbobenzoxy-L-prolyl-m-[di-(2-chlorethyl)amino]-L-phenylalanine-p-chloro-L-phenylalanine ethyl ester is obtained.

The protection group is eliminated, whereby one arrives at step E of schema 1, the end product being the L-prolyl-m-[di-(2-chlorethyl)amino]-L-alanine-p-fluoro-L-phenylalanine ethyl ester.

The reaction conditions are such as are used generally with peptide syntheses. With the above method, the end product is obtained with a yield of 30%, with respect to the starting product m-[di-(2-chlorethyl)amino]-L-phenylalanine ethyl ester, it being necessary to carry out the purification of at least one intermediate product through column chromatography on silica gel.

The method can actually be applied industrially, but it is relatively complicated and leads to a rather insufficient yield.

If one takes into consideration the properties of the end product PSF-hydrochloride, the realization of another method of production, which can easily be applied industrially and which results in a better yield than that of the state of the art, is then an extraordinarily important and interesting object of the present invention.

It has been found that the method for producing PSF according to the invention, which uses another reaction sequence, is superior to the state-of-the-art method.

The subject matter of the present invention is thus the method defined in claim 1 for producing L-prolyl-L-m-sarcolysyl-L-p-fluorophenylalanine and esters and/or salts thereof.

The method according to the invention takes place according to the following schema 2:

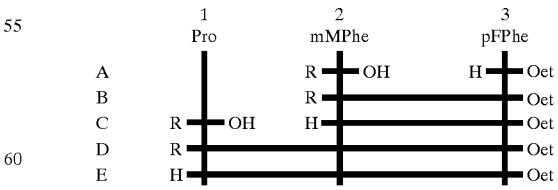

Pro = proline
mMPhe = m-[di(2-chlorethyl)]-amino-L-phenylalanine (=L-m-sarcolysine)
pFPhe = p-fluoro-L-phenylalanine
R = benzyloxycarbonyl, t-butoxycarbonyl (BOC) or 9-fluorenylmethyoxycarbonyl (Fmoc)

The method comprises the following process steps, which are indicated in schema 2 above:
a) condensation of R-m-[di-(2-chlorethyl)amino]-L-phenylalanine with p-fluoro-L-phenylalanine ethyl ester, whereby R-m-[di-2-chlorethyl)amino]-L-phenylalanyl-p-fluoro-L-phenylalanine ethyl ester is obtained;
b) Removal of the protection group R;
c) condensation of the product obtained in step b) with R-L-proline, R-L-prolyl-m-[di-(2-chlorethyl)amino]-L-phenylalanyl-p-fluoro-L-phenylalanine ethyl ester being obtained;
d) Removal of the protection group R and synthesis of the hydrochloride; R can be benzyloxycarbonyl, t-butyloxicarbonyl or 9-fluorenylmethoxycabonyl. R is preferably a benzyloxycarbonyl group.

The method according to the present invention shows a total yield of 50% with respect to the starting product R-m-[di-(2-chlorethyl)amino]-L-phenylalanine.

The method according to the present invention has a great advantage in carrying out the synthesis of the end product since crystalline intermediate products are obtained which can be purified extraordinarily easily through crystallization.

The features and the advantages of the method according to the invention will be explained, for better comprehension, in the following description. The tripeptide, produced according to the inventive method, is produced according to schema 2 above. Therein R is a benzyloxycarbonyl or a t-butoxycarbonyl group (BOC) or a 9-fluorenylmethoxycarbonyl group (Fmoc).

As follows from schema 2, the method calls for, in step A, the condensation of R-m-[di-2-chlorethyl)amino]-L-phenylalanine with the ethyl ester of the p-fluorophenylalanine, the corresponding protected tripeptide being obtained in step B.

In step C, the benzyloxycarbonyl group is removed, and through a condensation of the R-L-proline with m-[di-(2-chlorethyl)amino]-L-phenylalanyl-p-fluoro-L-phenylalanine ethyl ester, the R-L-prolyl-m-[di-2-chlorethyl)amino]-L-phenylalanyl-p-fluoro-L-phenylalanine ethyl ester is obtained in step D of schema 2.

The protection group R is removed in step E of schema 2, the end product being L-prolyl-m-[di-(2-chlorethyl)amino]-phenylalanyl-p-fluoro-phenylalanine ethyl ester.

The reaction conditions are such as are generally standard with peptide synthesis.

The peptide L-prolyl-m-sarcolysyl-L-p-fluorophenylalanin (PSF) is produced preferably in the form of hydrochlorides or hydrobromides.

The following example serves the purpose of elucidation of the present invention.

EXAMPLE

Synthesis of L-prolyl-L-m-sarcolysyl-L-p-fluorophenylalanine ethyl ester hydrochloride a) N-carbobenzoxy-L-m-sarcolysyl-L-D-fluorophenylalanine ethyl ester 52.5 g of L-p-fluorophenylalanine ethyl ester hydrochloride are treated with 75 ml of $Na_2CO_3$ (sodium carbonate) saturated solution and 150 ml of $CHCl_3$. The mixture is shaken out, and the organic phase is separated and saved. The aqueous phase is shaken out a second time with 75 ml of $CHCl_3$. The combined chloroform extracts are mixed and washed once with water, and then separated from the aqueous phase and dried on anhydrous $Na_2SO_4$. The concentration of amino acid ester is determined by a titration with $HClO_4$ (perchloric acid). The yield corresponds approximately to the theoretical value; it is at 98%.

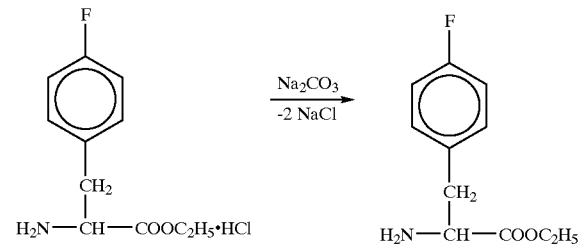

286.5 ml of a chloroform solution containing 0.1905 moles of L-p-fluorophenylalanine ethyl ester are reacted with 83.7 g (0.1905 moles) of N-cbzo-L-m-sarcolysine. The solution is cooled on an ice bath.

Added to the cooled solution with stirring are 41.25 g (0.200 moles of dicyclohexyl carbodiimide—DCC) and 60 ml of chloroform, the solution being constantly stirred with simultaneous cooling for 30 min. The mixture may possibly solidify into a solid mass. In this case, the mass is made liquid again through addition of 150 ml of chloroform, it being stirred with slight warming. In this way, dissolving of the precipitated product is accelerated. The reaction is ended 2 hrs after addition of the DDC. The end of reaction is established by TLC checking (thin-layer chromatography; silica gel G layer, solvent: chloroform+acetone 9:1, manifestation by spraying with dilute, acid $KMnO_4$ solution). The precipitated dicyclohexyl urea is separated by filtration. The solution is washed first with little water, then with saturated $Na_2CO_3$ solution. The chloroform solution is shaken out once more with water and then dried with Na2SO4. The solvent is evaporated in vacuo and removed. After drying, 140.25 g of slightly yellowish-colored product is obtained (yield 98.3%). The substance produced has a melting point of 123–124.5° C. and is chromatographically homogeneous. Through crystallization of 4.5 g of substance from 37.5 ml ethyl alcohol, 3.75 g of a lighter product are produced with a melting point of 125–126° C. $\alpha_D^{20}$:27.7 (c=2, $CHCl_3$).

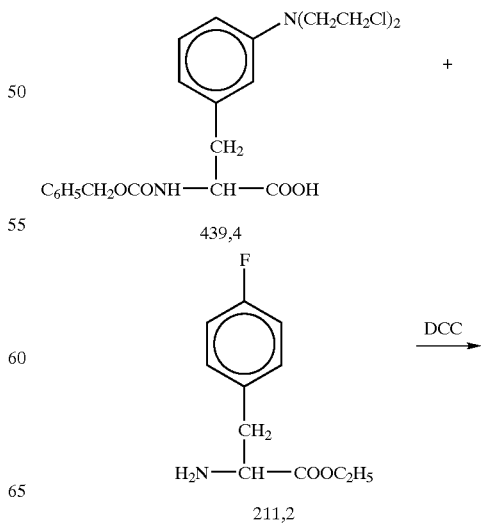

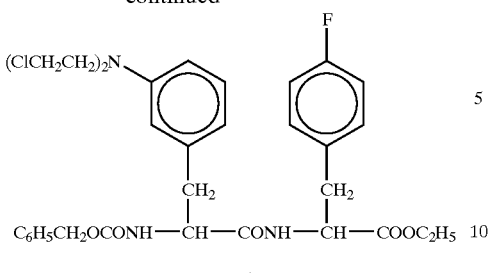

632,5

Analysis for $C_{32}H_{36}Cl_2FN_3O_5$
N% = 6.67(6.66 calculated
Cl% = 11.5 (calculated = 11.2)

b) L-m-sarcolysyl-L-p-fluorophenylalanine ethyl ester

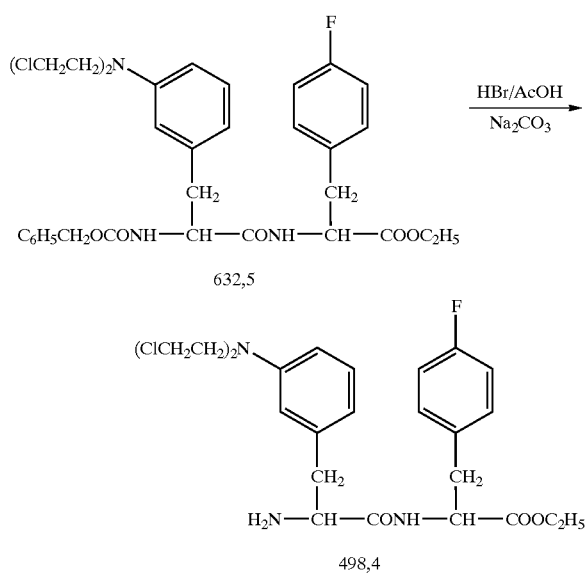

With exclusion of atmospheric humidity, 600 ml of HBr in glacial acetic acid (33%) are added with slow stirring to 390 g (0.616 moles) of die[?] M <sic. N->-carbobenzoxy-L-m-sarcolysyl-L-p-fluorophenylalanine ethyl ester. Dissolving and cessation of the $CO_2$ development takes place after 40 minutes. It is allowed to stand for a further 20 minutes with stirring and diluted with approx. 400 ml of ether. The whole is poured into 5 lt of ether which is kept under constant stirring, is decanted, and the precipitated oil is washed twice with 2 lt of ether with decanting. The oil is treated with 4 lt of water with stirring, and a solid is obtained, which is collected after approx. 30 min. by filtration, and is completely washed with a total of 1500 ml of water and 500 ml of ether. The bromohydrate thus obtained is suspended in 2 lt of ethyl acetate and treated with stirring with 450 ml of saturated sodium carbonate solution, thus until the solution is alkaline. After dissolving has taken place, filtration is carried out on the suction filter in order to remove the suspended dicyclohexyl urea (very little). In a separating funnel, the organic layer is separated from the aqueous phase, and the aqueous phase is extracted with a further 500 ml of ethyl acetate. The purified extracts are washed with 300 ml of water, $Na_2CO_4$ dried, and treated with norite. Filtration is carried out, and the filtrate is dried in vacuo (40° C.). The residue is taken up even before it becomes firm in 500 to 1000 ml of ether. During the night, a white product is precipitated from the solution obtained. Yield: 247 g (80.4%) Melting point 100–102° C.

$\alpha_D^{20}$=−7.5° (c=2, chloroform).

TLC (BuOH/AcOH/$H_2O$ 65:15:25; $KMnO_4$ diluted): one band, Rf=0.74.

analysis for $C_{24}H_{30}Cl_2FN_3O_3$.
N%=8.34 (8.43 calculated).
Cl%=14.1 (14.2 calculated).

c) N-carbobenzoxy-L-prolyl-L-m-sarcolysyl-L-p-fluorophenylalanine ethyl ester

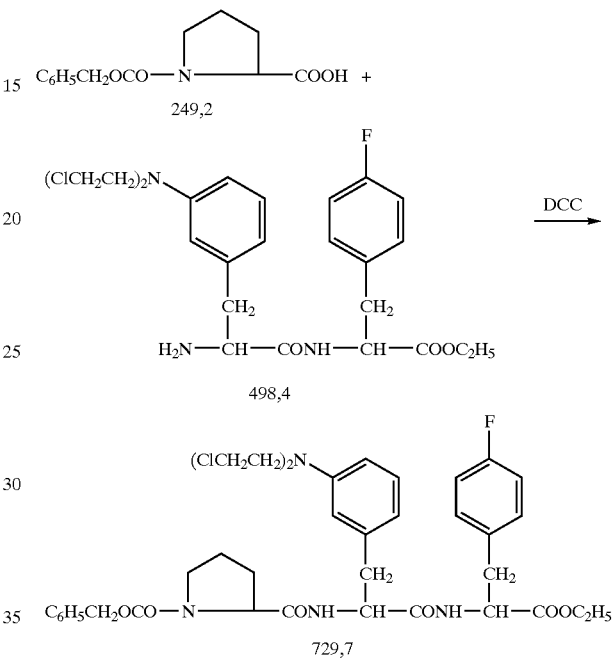

A mixture of 249 g (0.5 moles) of L-m-sarcolysyl-L-p-fluorophenylalanine ethyl ester, 125 g (0.5 moles) of N-cbzo-L-proline, and 109 g (0.525 moles) DCC in 3000 ml of chloroform is allowed to stand for 30 minutes with stirring, with external cooling for a further 90 minutes at room temperature (TLC, silica gel G, Chf/$Me_2CO$ 9:1; or with BuOH/AcOH/$H_2O$ 65:15:25; $KMnO_4$, diluted, acid). After removal of the dicyclohexyl urea by filtration, the solvent is evaporated off in vacuo, and the residue, still in liquid state, is poured into 800 ml of ether. From the solution obtained, the product precipitates slowly out, which is collected on a filter. Yield 290 g (78.5%). Melting point= 148–150° C., $\alpha_D^{20}$=−42.4° (c=2; chloroform)

Analysis for $C_{37}H_{43}FCl_2N_4O_6$.
N%=7.78% (7.68 calculated).
Cl%=9.6 (9.7 calculated).

d) L-prolyl-L-m-sarcolysyl-L-p-fluorophenylalanine ethyl ester hydrochloride

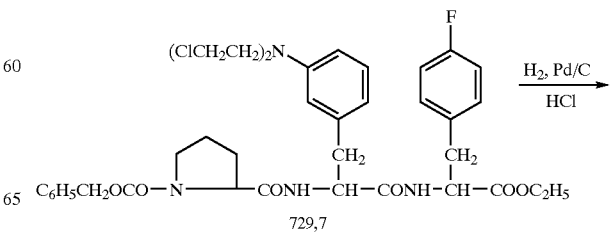

-continued (ClCH$_2$CH$_2$)$_2$N—[m-phenyl]—CH$_2$—;  F—[p-phenyl]—CH$_2$—

HN—[pyrrolidine]—CONH—CH—CONH—CH—COOC$_2$H$_5$ · HCl

632

A mixture of 157.5 (0.261 moles) N-carbobenzoxy-L-prolyl-L-m-sarcolysyl-L-p-fluorophenylalanine ethyl ester and 30 g of palladium on 5% carbon is suspended under a stream of nitrogen in 15 ml of glacial acetic acid and 1750 ml of methanol. The reaction mixture is kept stirred and is reduced under a stream of hydrogen. After termination of the CO$_2$ development (after 4–5 hours), a TLC chromatography check is carried out (silica gel G), elution taking place with chloroform acetone 9:1 and making visible with dilute KMnO$_4$.

After removal of the catalyst by filtration, the filtrate is acidified with concentrated ethanolic HCl in a stoichiometric amount or a little more. The white, crystalline precipitate which slowly forms is collected on a filter and washed with ethanol or with ether: 85 g. The filtrate is concentrated practically to dryness, and the residue is recrystallized from ethanol: 25 g. Complete yield: 110 g (80.5%); melting point 122–124° C. (modification of the aggregate state)

$\alpha_D^{20}$=13.0°±0.5 (c=2; MeOH).

TLC (silica gel G; BuOh/AcOH/H$_2$O 65:15:25; KMnO$_4$ diluted: one band Rf=0.54.

Analysis for C$_{29}$H$_{38}$Cl$_3$FN$_4$O$_4$.

N%=8.93% (8.86 calculated).

Cl%=16.7% (16.8 calculated).

Cl-%=5.65% (5.6 calculated).

What is claimed is:

1. A method of producing at least one member of the group consisting of L-prolyl-L-m-sarcolysyl-L-p-fluorophenylalanine, a lower alkyl ester thereof and acid addition salts thereof, wherein L-p-fluorophenylalanine with a protected carboxyl group is caused to react with L-m-sarcolysine with a protected amino group and an activated carboxy group, L-m-sarcolysyl-L-p-fluorophenylalanine with a protected amino group and with a protected carboxy group being obtained, and subsequently the amino protection group is removed, afterwards the obtained L-m-sarcolysyl-L-p-fluorophenylalanine with a protected carboxy group is caused to react with proline with a protected amino group and an activated carboxy group, L-prolyl-L-m-sarcolysyl-L-p-fluorophenylalanine with a protected amino group being obtained, and the amino protection group being removed, and the lower alkyl ester group being optionally removed or converted into another ester group and/or the compound obtained being converted into an acid addition salt.

2. The method according to claim 1, wherein the condensation is carried out with cooling in an anhydrous medium.

3. The method according to claim 1, wherein the activated carboxy groups were activated through treatment with dicyclohexylcarbodiimid.

4. The method according to claim 1, wherein the carboxy protection group of L-p-fluorophenylalanine is a lower alkyl ester group.

5. The method according to claim 1, wherein the amino protection group of the L-m-sarcolysine is a carbobenzoxy group.

6. The method according to claim 1, wherein the removal of the amino protection group of the L-m-sarcolysyl-L-p-fluorophenylalanine with a protected amino group is carried out through treatment with hydrogen bromide in glacial acetic acid.

7. The method according to claim 1, wherein the removal of the amino protection group of the L-prolyl-L-m-sarcolysyl-L-p-fluorophenylalanine with a protected amino group is carried out through reduction with hydrogen in the presence of palladium on carbon.

8. The method according to claim 2, wherein the condensation is carried out with cooling in chloroform.

9. The method according to claim 1, wherein the carboxy protection group of L-p-fluorophenylalanine is an ethyl ester group.

10. The method according to claim 2, wherein the activated carboxy groups were activated through treatment with dicyclohexylcarbodiimide.

11. The method according to claim 2, wherein the carboxy protection group of L-p-fluorophenylalanine is a lower alkyl ester group.

12. The method according to claim 2, wherein the amino protection group of the L-m-sarcolysine is a carbobenzoxy group.

13. The method according to claim 2, wherein the removal of the amino protection group of the L-m-sarcolysyl-L-p-fluorophenylalanine with a protected amino group is carried out through treatment with hydrogen bromide in glacial acetic acid.

14. The method according to claim 2, wherein the removal of the amino protection group of the L-prolyl-L-m-sarcolysyl-L-p-fluorophenylalanine with a protected amino group is carried out through reduction with hydrogen in the presence of palladium on carbon.

* * * * *